(12) United States Patent
Karakaya et al.

(10) Patent No.: US 11,724,247 B2
(45) Date of Patent: Aug. 15, 2023

(54) BIFUNCTIONAL CATALYSTS AND SYSTEMS AND METHODS FOR OXIDATIVE DEHYDROGENATION OF ALKANES TO OLEFINS AND HIGH-VALUED PRODUCTS

(71) Applicants: Canan Karakaya, Knoxville, TN (US); Robert J. Kee, Arvada, CO (US); Olaf Deutschmann, Linkenheim-Hochstetten (DE)

(72) Inventors: Canan Karakaya, Knoxville, TN (US); Robert J. Kee, Arvada, CO (US); Olaf Deutschmann, Linkenheim-Hochstetten (DE)

(*) Notice: Subject to any disclaimer, the term of this patent is extended or adjusted under 35 U.S.C. 154(b) by 0 days.

(21) Appl. No.: 17/207,323

(22) Filed: Mar. 19, 2021

(65) Prior Publication Data

US 2021/0291150 A1 Sep. 23, 2021

Related U.S. Application Data

(60) Provisional application No. 62/992,692, filed on Mar. 20, 2020.

(51) Int. Cl.
*B01J 23/26* (2006.01)
*B01J 23/00* (2006.01)
*B01J 6/00* (2006.01)
*C07C 5/48* (2006.01)
*C01B 3/40* (2006.01)

(52) U.S. Cl.
CPC ............... *B01J 23/26* (2013.01); *B01J 6/001* (2013.01); *B01J 23/002* (2013.01); *C01B 3/40* (2013.01); *C07C 5/48* (2013.01)

(58) Field of Classification Search
CPC . B01J 23/26; B01J 6/001; B01J 23/002; B01J 23/22; B01J 23/08; B01J 23/745; C01B 3/40; C97C 5/48; C07C 5/48
USPC ....... 502/319, 312, 314, 316, 320, 336, 338, 502/353, 354; 585/654, 662
See application file for complete search history.

(56) References Cited

U.S. PATENT DOCUMENTS

| | | | | |
|---|---|---|---|---|
| 2005/0113247 A1* | 5/2005 | Chen | .................... | B01J 23/8926 502/200 |
| 2006/0013759 A1* | 1/2006 | Jiang | ....................... | C01B 3/384 423/648.1 |
| 2016/0237002 A1* | 8/2016 | Vestre | ...................... | B01J 29/48 |

FOREIGN PATENT DOCUMENTS

| | | | | |
|---|---|---|---|---|
| CA | 2497441 C | * | 11/2013 | ............. B01B 1/005 |
| EP | 0832056 B1 | * | 5/2001 | ............... C07C 5/42 |

OTHER PUBLICATIONS

Hikaru Saito et al., "Dehydrogenation of Ethane via the Mars-van Krevelen Mechanism over La0.8Ba0.2-MnO3-δ Perovskites under Anaerobic Conditions." Journal of Physical Chemistry C, 123, pp. 26272-26281. (Year: 2019).*

(Continued)

*Primary Examiner* — Patricia L. Hailey
(74) *Attorney, Agent, or Firm* — Sheridan Ross P.C.

(57) ABSTRACT

Bifunctional catalyst compositions, methods, and systems are provided for the use of $CO_2$ as a soft oxidizing agent to effectively convert low-value small alkanes to high-value small olefins. The bifunctional catalyst comprises a metal oxide catalyst and a redox-active ceramic support.

18 Claims, 6 Drawing Sheets

(56) References Cited

OTHER PUBLICATIONS

Agafonov et al., "Propane Dehydrogenation on Chromium Oxide and Gallium Oxide Catalysts in the Presence of CO2," Kinetics and Catalysts, vol. 59, No. 6, 2018, pp. 744-753.

Atanga et al., "Oxidative dehydrogenation of propane to propylene with carbon dioxide," Applied Catalysis B: Environmental, vol. 220, 2018, pp. 429-445.

Duan et al., "Highly durable, coking and sulfur tolerant, fuel-flexible protonic ceramic fuel cells," Nature, vol. 557, May 10, 2018, pp. 217-235.

El Hawa et al., "Application of a Pd—Ru composite membrane to hydrogen production in a high temperature membrane reactor," Separation and Purification Technology, vol. 147, Feb. 2015, pp. 388-397.

Jennings et al., "Measurement and Characterization of a High-Temperature, Coke-Resistant Bi-functional Ni/BZY15 Water-Gas-Shift Catalyst Under Steam-Reforming Conditions," Catalysis Letters, vol. 148, Oct. 5, 2018, pp. 3592-3607.

Nowicka et al., "Elucidating the Role of CO2 in the Soft Oxidative Dehydrogenation of Propane over Ceria-Based Catalysts," ACS Catalysis, vol. 8, Mar. 13, 2018, pp. 3454-3468.

Yan et al., "Active sites for tandem reactions of CO2 reduction and ethane dehydrogenation," PNAS, vol. 115, No. 33, Aug. 14, 2018, pp. 8278-8283.

Zhang et al., "Efficient Ammonia Decomposition in a Catalytic Membrane Reactor to Enable Hydrogen Storage and Utilization," ACS Sustainable Chemistry and Engineering, vol. 7, Feb. 27, 2019, pp. 5975-5985.

Zhu et al., "Defect Chemistry and Transport within Dense BaCe0.7Zr0.1Y0.1Yb0.1O3-δ (BCZYYb) Proton-Conducting Membranes," Journal of The Electrochemical Society, vol. 165, No. 10, Jul. 25, 2018, pp. F845-F853.

Zhu et al., Defect Incorporation and Transport within Dense BaZr0.8Y0.2O3-δ (BZY20) Proton-Conducting Membranes, Journal of the Electrochemical Society, vol. 165, No. 9, May 26, 2018, pp. F581-F588.

\* cited by examiner

BIFUNCTIONAL CATALYSTS AND SYSTEMS AND METHODS FOR OXIDATIVE DEHYDROGENATION OF ALKANES TO OLEFINS AND HIGH-VALUED PRODUCTS

CROSS REFERENCE TO RELATED APPLICATIONS

This application claims the benefit of priority under 35 U.S.C. § 119(e) to U.S. Provisional Patent Application 62/992,692 filed Mar. 20, 2020, the entirety of which is incorporated herein by reference.

FIELD OF THE INVENTION

The present disclosure relates to bifunctional catalysts and systems and methods for the oxidative dehydrogenation of alkanes using carbon dioxide as a soft oxidant.

BACKGROUND

Natural gas typically contains significant levels of ethane (up to 9%) and propane (up to 1.5%), which must be separated prior to processes such as steam methane reforming (SMR). Due to the low heating value and separation costs, the $C_2$ and $C_3$ compounds are often simply flared. However, these byproducts could be converted to light olefins, serving as the feedstock for producing a vast array of high-value chemicals, including polymers (e.g., polyethylene and polypropylene), oxygenates (e.g., ethylene glycol, acetaldehyde, acetone, and propylene oxide), and important chemical intermediates (e.g., ethylbenzene and acrylonitrile).

Olefins are conventionally produced from naphtha by either catalytic or steam cracking. Catalytic cracking requires high temperatures, is thermodynamically (equilibrium) limited, and requires frequent catalyst regeneration due to catalyst-fouling and coke formation. Conventional oxidative dehydrogenation (ODH) of alkanes tends to avoid coke formation, but has poor olefin yield due to competition with the thermodynamically favored complete oxidation reaction (e.g., reactions 1 and 2):

$$C_3H_8 + 5O_2 \rightarrow 3CO_2 + 4H_2O; \text{ and} \quad (1)$$

$$C_2H_6 + 3.5O_2 \rightarrow 2CO_2 + 3H_2O. \quad (2)$$

ODH processes using $CO_2$ as a mild oxidant have been reported. Most of the prior research has focused on catalyst development, seeking to improve selectivity for olefin production compared to cracking. These processes typically require temperatures in the range of 450° C.≤T≤700° C. to achieve significant conversion and an excess supply of $CO_2$ to mitigate coke formation. To date, metal oxides such as $Cr_2O_3$ and $V_2O_5$ are known to be selective for ODH processes, but catalyst stability remains a concern. For instance, for propane ODH, the feed gas typically contains reactant mixtures in the range of $1 \leq CO_2/C_3H_8 \leq 10$ and the resulting $C_3H_6$ formation rates are reported to be low due to low Weight Hourly Space Velocity (WHSV≤1000 alkane (ml) gcat$^{-1}$ h$^{-1}$). A $C_3H_6$ yield of 45% over a $Cr_2O_3$/silica catalyst has been reported, but the net $C_3H_6$ formation rates were very low, in the range of micromole olefin gcat$^{-1}$ h' and, after only a few hours of operation, the catalyst was severely deactivated. This information is set forth in: B. Yan, S. Yao, S. Kattel, Q. Wu, Z. Xie, E. Gomez, P. Liu, D. Su, and J. G. Chen, "Active sites for tandem reactions of $CO_2$ reduction and ethane dehydrogenation," *PNAS*, 115: 8278-8283, 2018; M. A. Atanga, F. Rezaei, A. Jawad, M. Fitch, and A. A. Rownaghi, "Oxidative dehydrogenation of propane to propylene with carbon dioxide," *Appl. Catal. B*, 220:428-445, 2018; Yu. A. Agafanow, N. A. Gaidai, and A. L. Lapidis, "Propane dehydrogenation on chromium oxide and gallium oxide catalysts in the presence of $CO_2$," *Kinetics Catal.*, 59: 744-753, 2018; and E. Nowicka, C. Reece, S. M. Althahban, K. M. H Mohammed, S. A. Kon drat, D. J. Morgan, Q. He, D. J. Willock, S. Golunski, C. J. Kiely, and G. J. Hutchings, "Elucidating the role of $CO_2$ in the soft oxidative dehydrogenation of propane over ceria-based catalysts," *ACS Catal.*, 8:3454-3468, 2018 (each of which are incorporated herein by reference in their entirety). Accordingly, there is a need in the art for new redox active catalysts and for methods for oxidative dehydrogenation of alkanes.

SUMMARY

The present invention relates to oxidative dehydrogenation (ODH) catalysts and methods and systems that use $CO_2$ as a soft oxidizing agent to effectively convert low-value small alkanes to high-value small olefins. A significant improvement of ODH process is provided based on the design and development of dehydrogenation catalysts that are highly olefin selective, cost effective, and coke-free. The catalysts disclosed herein are bifunctional catalysts, combining metal oxide catalysts with redox-active ceramic supports. The disclosed methods and systems benefit from the synergistic interactions of three material processes: 1) a redox-active metal oxide catalyst that produces olefins from alkanes according to a Mars van Krevelen (MvK) cycle; 2) a redox-active ceramic support that promotes water-gas-shift (WGS) chemistry; and 3) a hydrogen-selective membrane that removes $H_2$ from the catalyst bed.

Figure 1:
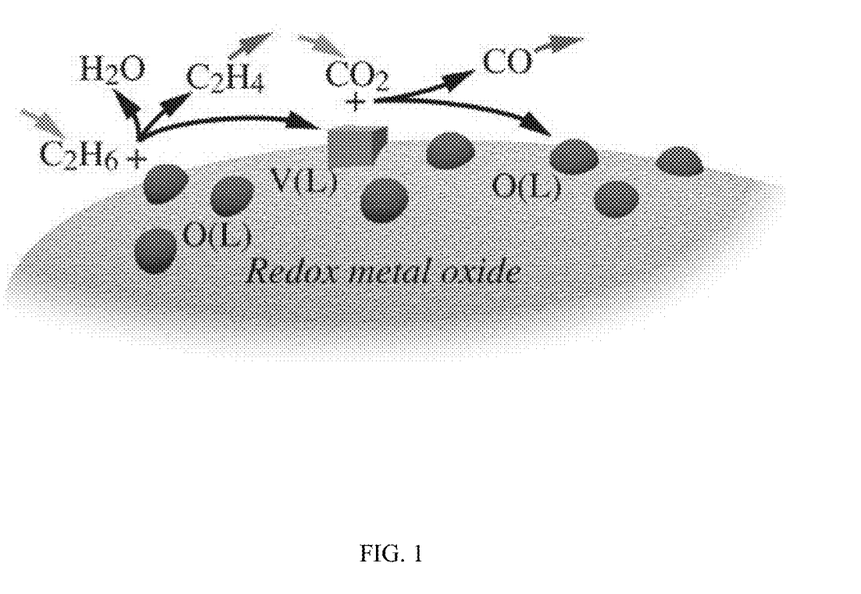
FIG. 1: A schematic representation of MvK oxidative dehydrogenation over a redox active metal oxide catalyst.

The bifunctional catalyst comprises a metal oxide catalyst which reduces alkanes to olefins via a MvK process using carbon dioxide as a soft oxidant. FIG. 1 is an illustration that shows the central aspects of the MvK process. Alkanes are reduced on the surface of the metal oxide catalyst, forming olefins and water. Carbon dioxide re-activates the metal oxide surface. This process depends on the ability of the metal to change oxidation state to accommodate a vacancy formation. Initially, atomic oxygen from the crystal lattice (O(L)) abstracts hydrogen from the paraffin to produce the olefin, releasing gas-phase $H_2O$ and leaving an oxygen vacancy (V(L)) in the lattice, $$C_2H_{2n+2} + O(L) \rightarrow C_nH_{2n} + V(L) + H_2O. \quad (3)$$

Gas-phase $CO_2$ then re-oxidizes the lattice vacancy, releasing CO and closing the catalytic cycle, $$CO_2 + V(L) \rightarrow CO + O(L). \quad (4)$$

The net reaction is, $$C_2H_{2n+2} + CO_2 \rightarrow C_nH_{2n} + CO + H_2O. \quad (5)$$

Although the net representation of the ODH process shows the stoichiometric dependency of the alkane conversion to $CO_2$, the optimum alkane/$CO_2$ ratio depends greatly on the particular metal-oxide and support material and their interactions. Beyond the desired reaction pathway, side reactions can affect the overall process yield. For instance, the ODH reaction competes with the non-oxidative dehydrogenation of the alkane on the metal oxide surface, which also produces an olefin, $$C_2H_{2n+2} \leftrightarrows C_2H_{2n} + H_2. \quad (6)$$

The redox-active ceramic support promotes the conversion of CO and $H_2O$, which are produced from the ODH of alkanes, to form $CO_2$ and $H_2$ via the WGS reaction, $$CO + H_2O \leftrightarrows CO_2 + H_2. \quad (7)$$

Figure 2:
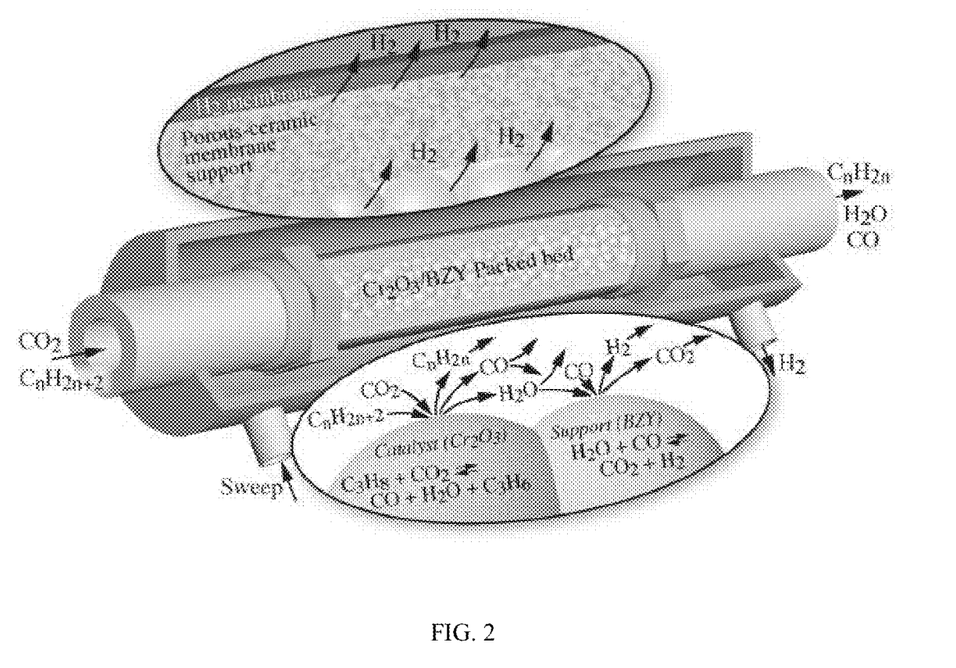
FIG. 2: A schematic representation of a catalytic membrane reactor (CMR) using a packed catalyst bed. The inset is a schematic representation of MvK oxidative dehydrogenation and WGS processes over the bifunctional catalyst.

The WGS activity beneficially removes the unwanted co-product CO, increases the olefin selectivity, and produces $H_2$ as a valuable reaction product. $CO_2$ is regenerated and reacts via equation 4 to produce more lattice oxygen, and the consumption of CO is expected to shift the equilibrium of reaction 4 to produce more lattice oxygen. This synergistic process is shown in the inset of FIG. 2. In addition to having WGS activity, the redox-active ceramic support beneficially contributes to coke mitigation to extended catalyst lifetime or stability. The removal of CO via the WGS also mitigates coke formation via the Boudouard reaction, $$2CO \rightarrow C_{(s)} + CO_2. \quad (8)$$

The $H_2$ produced by the WGS reaction, and also through non-oxidative dehydrogenation of alkanes on the metal oxide surface (reaction 6), is preferably removed from the catalyst bed. When $CO_2$ and $H_2$ coexist, especially in high concentrations, the reverse Water Gas Shift (rWGS) (i.e., the reverse of reaction 7) is favored, which impedes the ODH chemistry. A $H_2$-selective membrane reactor can be used to remove $H_2$ from the gas-phase pore volume of the catalyst bed. In addition to improving ODH, the separated pure $H_2$ is also a valuable product.

An aspect of the invention is a bifunctional oxidative dehydrogenation catalyst (referred to herein as a bifunctional catalyst) comprising a metal oxide and a redox active ceramic support, wherein the redox active ceramic support promotes a water-gas shift process. The metal oxide may promote alkane dehydrogenation via a Mars van Krevelen process with carbon dioxide as an oxidant.

In some embodiments, the metal oxide is selected from the group consisting of $Cr_2O_3$, $V_2O_5$, $In_2O_3$, $Fe_2O_3$, and combinations thereof. The metal oxide may be mixed with or impregnated in the redox active ceramic support.

In some embodiments, the redox active ceramic support comprises one or more of $Al_2O_3$, $Ce_2O_3$, $ZrO_2$, $BaCe_{0.7}Zr_{0.1}Y_{0.1}Yb_{0.1}O_{2.95}$, and $BaZr_{1-x}Y_xO_{3-\delta}$ ($0 \leq x \leq 0.20$). In preferred embodiments, the redox active ceramic support comprises a doped perovskite ceramic. In some embodiments, doped perovskite ceramic is selected from the group consisting of $BaCe_{0.7}Zr_{0.1}Y_{0.1}Yb_{0.1}O_{2.95}$, $BaZr_{1-x}Y_xO_{3-\delta}$ ($0 \leq x \leq 0.20$), and combinations thereof.

Another aspect of the invention is a method for alkane dehydrogenation, comprising: providing a catalytic membrane reactor comprising a catalyst bed and a hydrogen selective membrane, wherein the catalyst bed comprises the bifunctional catalyst disclosed herein; contacting an input gas stream comprising at least one alkane and carbon dioxide with the bifunctional catalyst to form a product gas stream comprising at least one olefin and hydrogen; and separating hydrogen from the product gas stream.

In some embodiments, the at least one alkane comprises ethane, propane, butane, or mixtures thereof.

In some embodiments, alkane dehydrogenation occurs at least partially via a Mars van Krevelen process and a water-gas shift process forms at least some of the carbon dioxide.

In some embodiments, a molar ratio of the at least one alkane to carbon dioxide in the input gas stream is greater than 1.

In some embodiments, the input gas stream comprising $CO_2$ and at least one alkane is contracted with the bifunctional catalyst a temperature from about 450° C. to about 550° C.

In some embodiments, the hydrogen selective membrane comprises a material selected from the group consisting of a metal, a ceramic, a polymer, and combinations thereof. In some embodiments, the hydrogen selective membrane comprises Pd or Pd alloys that are supported in porous-ceramic structures. In some embodiments, the hydrogen selective membrane is a protonic ceramic membrane.

In some embodiments, a rate of olefin production is about $1.0 \times 10^{-2}$ mol gcat$^{-1}$ h$^{-1}$ or more.

Another aspect of the invention is a catalytic membrane reactor comprising: the bifunctional catalyst disclosed herein; and a hydrogen selective membrane, wherein the bifunctional catalyst is contained in a catalyst bed that is at least partially enclosed by the hydrogen selective membrane. In some embodiments, the catalytic membrane reactor further comprises an input gas stream comprising $CO_2$ and at least one alkane and first and second output gas streams, the first output gas stream comprises at least one olefin and the second output gas stream comprises hydrogen. In some embodiments, the reactor further comprises a means for controlling and/or measuring one or more of input gas flow rates, output gas flow rates, the temperature of the reactor, and the pressure of the reactor. In some embodiments, the reactor comprises a means for collecting the hydrogen gas stream and a means for collecting the olefins.

This summary is neither intended nor should it be construed as being representative of the full extent and scope of the present disclosure. The present disclosure is set forth in various levels of detail in the summary as well as in the attached drawings and the detailed description, and no limitation as to the scope of the present disclosure is intended by either the inclusion or non-inclusion of elements, components, etc. in this summary. Additional aspects of the present disclosure will become more readily apparent from the detailed description, particularly when taken together with the drawings.

The phrases "at least one," "one or more," "or," and "and/or" are open-ended expressions that are both conjunctive and disjunctive in operation. For example, each of the expressions "at least one of A, B and C," "at least one of A, B, or C," "one or more of A, B, and C," "one or more of A, B, or C," "A, B, and/or C," and "A, B, or C" means A alone, B alone, C alone, A and B together, A and C together, B and C together, or A, B and C together. When each one of A, B, and C in the above expressions refers to an element, such as X, Y, and Z, or class of elements, such as $X_1$-$X_n$, $Y_1$-$Y_m$, and $Z_1$-$Z_o$, the phrase is intended to refer to a single element selected from X, Y, and Z, a combination of elements selected from the same class (e.g., $X_1$ and $X_2$) as well as a combination of elements selected from two or more classes (e.g., $Y_1$ and $Z_o$).

The term "a" or "an" entity refers to one or more of that entity. As such, the terms "a" (or "an"), "one or more," and "at least one" can be used interchangeably herein. It is also to be noted that the terms "comprising," "including," and "having" can be used interchangeably.

Unless otherwise indicated, all numbers expressing quantities, dimensions, conditions, ratios, ranges, and so forth used in the specification and claims are to be understood as being modified in all instances by the term "about" or "approximately". Accordingly, unless otherwise indicated, all numbers expressing quantities, dimensions, conditions, ratios, ranges, and so forth used in the specification and claims may be increased or decreased by approximately 5% to achieve satisfactory results. In addition, all ranges described herein may be reduced to any sub-range or portion of the range.

The use of "including," "comprising," or "having" and variations thereof herein is meant to encompass the items listed thereafter and equivalents thereof as well as additional items. Accordingly, the terms "including," "comprising," or "having" and variations thereof can be used interchangeably herein.

It shall be understood that the term "means" as used herein shall be given its broadest possible interpretation in accordance with 35 U.S.C., Section 112(f). Accordingly, a claim incorporating the term "means" shall cover all structures, materials, or acts set forth herein, and all of the equivalents thereof. Further, the structures, materials, or acts and the equivalents thereof shall include all those described in the summary, brief description of the drawings, detailed description, abstract, and claims themselves.

BRIEF DESCRIPTION OF THE DRAWINGS

The accompanying drawings, which are incorporated in and constitute a part of the specification, illustrate embodiments of the disclosed system and together with the general description of the disclosure given above and the detailed description of the drawings given below.

FIG. 4: (A) Net $C_3H_6$ production rate and propane conversion and yield as a function of $C_3H_8/CO_2$ ratio at 600° C.; (B) $C_3H_8$ and $CO_2$ conversion and product selectivity as a function of temperature for a $C_3H_8/CO_2$ ratio of 2.5.

FIG. 5: (A) Impact of $H_2$ addition on propane conversion and propylene selectivity at GHSV=33,900 $h^{-1}$ and a $C_3H_8/CO_2$ ratio of 2.5; (B) $CO_2$ conversion as a function of temperature and $H_2/CO_2$ ratio.

DETAILED DESCRIPTION

An aspect of the invention is an oxidative dehydrogenation (ODH) catalyst for the conversion of low-value small alkanes to high-value small olefins using $CO_2$ as a soft oxidizing agent. The ODH catalyst is a bifunctional catalyst, comprising a metal oxide catalyst and a redox-active ceramic support.

The metal oxide catalyst component in the bifunctional catalyst converts alkanes to olefins according to a Mars van Krevelen (MvK) cycle using $CO_2$. Alkane dehydrogenation via $CO_2$ as a soft oxidant is known to proceed on redox-active metal oxide catalysts such as, by way of non-limiting example, $Cr_2O_3$, $V_2O_5$, $In_2O_3$, or $Fe_2O_3$. In some embodiments, the metal oxide may be a mixture of two or more metal oxides.

The redox-active ceramic support promotes water-gas-shift (WGS) chemistry. Suitable redox-active ceramic support materials are, by way of non-limiting example, alumina ($Al_2O_3$), $Ce_2O_3$, and $ZrO_2$. In preferred embodiments, the redox-active ceramic support is a doped-perovskite ceramic.

A general formula of a doped perovskite material may be $AB_xM_{1-x}O_{3-\delta}$, where x and $\delta$ represent cations molar ratio and oxygen-ion vacancy, respectively. Suitable doped-perovskite ceramics are, by way of non-limiting example, $BaCe_{0.7}Zr_{0.1}Y_{0.1}Yb_{0.1}O_{2.95}$, and $BaZr_{1-x}Y_xO_{3-\delta}$ (0≤x≤0.20) (BZY). It has previously been shown that some doped-perovskite ceramics (e.g., BZY) can avoid solid coke formation under ethane and propane steam-reforming environments. For example, in the presence of steam (an ODH byproduct), BZY becomes hydrated, providing surface hydroxyls. While not wishing to bound to a particular theory, these surface hydroxyls may spill over to the metal oxide catalyst to oxidize coke-precursors that may accumulate on the metal oxide. This information is set forth in: D. M. Jennings, C. Karakaya, H. Zhu, C. Duan, R. P. O'Hayre, G. S. Jackson, I. E. Reimanis, and R. J. Kee, "Measurement and characterization of a high-temperature, coke-resistant bi-functional Ni/BZY15 water-gas-shift catalyst under steam-reforming conditions," *Catal. Lett.*, 148:3592-3607, 2018; C. Duan, R. J. Kee, H. Zhu, C. Karakaya, Y. Chen, S. Ricote, A. Jarry, E. J. Crumlin, D. Hook, R. Braun, N. P. Sullivan, and R. P. O'Hayre, "Highly durable, coking and sulfur tolerant, fuel-flexible protonic ceramic fuel cells," *Nature*, 557:217-222, 2018; and Z. Zhang, S. Liguori, T. F. Fuerst, J. D. Way, and C. A. Wolden, "Efficient ammonia decomposition in a catalytic membrane reactor to enable hydrogen storage and utilization," *ACS Sust. Chem. Eng.*, 7:5975-5985, 2019 (each of which are incorporated herein by reference in their entirety). In some embodiments, the ceramic support may be a mixture of two or more ceramic support materials.

The bifunctional catalyst may be formed by known methods in the art. In some embodiments, the metal oxide is dispersed within the redox-active ceramic support by physically mixing the two materials together or the metal oxide may by impregnated into the ceramic support material. For instance, the bifunctional catalysts may be prepared by an incipient wetness impregnation technique using the corresponding metal nitrate or metal carbonate as a precursor, or using another suitable precursor, to form the metal oxide. A solution of the metal nitrate or metal carbonate precursor is prepared, the ceramic support is added to the solution and the mixture is diluted with water. The mixture is dried and then the metal oxide/ceramic support mixture is calcinated to remove any residual solvent and convert the metal nitrate or metal carbonate to a metal oxide. The calcination temperature depends upon the specific metal nitrate. Typical calcination temperatures range from about 450° C. to about 650° C., preferably 500° C. to about 600° C., and may be performed in air for several hours (e.g., 4-7 hours).

In some embodiments, the bifunctional catalyst comprises less than about 50 wt. % of the redox-active metal oxide catalyst, less than about 45 wt. % of the redox-active metal oxide catalyst, less than about 40 wt. % of redox-active metal oxide catalyst, less than about 35 wt. % of the redox-active metal oxide catalyst, less than about 30 wt. % of the redox-active metal oxide catalyst, less than about 25 wt. % of the redox-active metal oxide catalyst, less than about 20 wt. % of the redox-active metal oxide catalyst, less than about 15 wt. % of the redox-active metal oxide catalyst, or less than about 10 wt. % of the redox-active metal oxide catalyst. In some embodiments, the bifunctional catalyst comprises at least 1 wt. % of the redox-active metal oxide catalyst, or at least 5 wt. % of the redox-active metal oxide catalyst. In some embodiments, the bifunctional catalyst comprises about 50 wt. % of the redox-active metal oxide catalyst, about 45 wt. % of the redox-active metal oxide catalyst, about 40 wt. % of the redox-active metal oxide catalyst, about 35 wt. % of the redox-active metal oxide catalyst, about 30 wt. % of the redox-active metal oxide catalyst, about 25 wt. % of the redox-active metal oxide catalyst, about 20 wt. % of the redox-active metal oxide catalyst, about 15 wt. % of the redox-active metal oxide catalyst, about 10 wt. % of the redox-active metal oxide catalyst, about 5 wt. % of the redox-active metal oxide catalyst, or about 1 wt. % of the redox-active metal oxide catalyst, or any range within any two of these values. In preferred embodiments, the bifunctional catalyst comprises between about 5 wt. % to about 20 wt. % of the redox-active metal oxide catalyst. In embodiments, the bifunctional catalyst comprises between about 1 wt. % to about 50 wt. %, preferably about 5 wt. % to about 20 wt. %, of the redox-active metal oxide catalyst, with the remainder of the bifunctional catalyst consists essentially of the redox-active ceramic support.

Another aspect of the present invention is a method for ODH of alkanes. In some embodiments, the alkane is ethane, propane, and/or butane, although larger alkanes may also be reduced. In some embodiments, the alkane is a $C_2$-$C_6$ alkane or a mixture thereof. The method for alkane dehydrogenation comprises contacting an input gas stream comprising at least one alkane and carbon dioxide with the bifunctional catalyst to form a product gas stream comprising the corresponding olefin(s). The product gas stream may further comprise water, carbon monoxide, carbon dioxide, and hydrogen as reaction products. Water and carbon monoxide are produced from the ODH of alkanes, and the GWS process converts these products to carbon dioxide and hydrogen (reaction 7). Hydrogen may also be formed from non-oxidative reduction of alkanes on the metal oxide catalyst (reaction 6). The formation of carbon dioxide is beneficial as it is used as a reactant in the MvK process. The formation of hydrogen, however, may impede the overall process by shifting the GWS reaction towards the reactants. Because of this, in preferred embodiments, hydrogen is removed from the product gas, for example using a hydrogen selective membrane.

In some embodiments, the method for alkane dehydrogenation, comprises: providing a catalytic membrane reactor (CMR) comprising a catalyst bed and a hydrogen selective membrane, wherein the catalyst bed comprises the bifunctional catalyst; contacting an input gas stream comprising at least one alkane and carbon dioxide with the bifunctional catalyst to form a product gas stream comprising the corresponding olefin(s); and separating hydrogen from the product gas stream. The product olefin(s) may be captured and purified down stream of the reactor.

In some embodiments, the input gas stream is contact with the bifunctional catalyst at a temperature in the range of about 450° C. to about 700° C. In some embodiment, the input gas stream is contact with the bifunctional catalyst at a temperature of about 450° C., about 475° C., about 500° C., about 525° C., about 550° C., about 575° C., about 600° C., about 625° C., about 650° C., about 675° C., or about 700° C., or any range within any two of these values. In general, the rate of the ODH reactions increase with increasing temperature; however, at higher temperatures the olefin product(s) dehydrogenate to form coke or polyaromatic hydrocarbons (PAHs) which are detrimental for the catalyst stability. Removal of hydrogen from the catalyst bed helps to mitigate or alleviate the formation of undesirable coke and PAHs. In embodiments where hydrogen is removed from the product gas, the temperature may be lower, compared to cases where hydrogen is not removed, typically the temperature may be in the range of about 450° C. to about 550° C.

The ratio of alkane to $CO_2$ in the input stream may impact the alkane conversion and olefin production rate. In some embodiments, the input stream has a ratio of alkane/$CO_2$ of less than about 1 (i.e., lean condition). In other embodiments, the amount of alkane/$CO_2$ is greater than about 1 (i.e., rich condition). In some embodiments, the input stream has a ratio of alkane/$CO_2$ of less than about 3.0, less than about 2.9, less than about 2.8, less than about 2.7, less than about 2.6, less than about 2.5, less than about 2.4, less than about 2.3, less than about 2.2, less than about 2.1, less than about 2.0, less than about 1.9, less than about 1.8, less than about 1.7, less than about 1.6, less than about 1.5, less than about 1.4, less than about 1.3, less than about 1.2, less than about 1.1, less than about 1.0, less than about 0.9, less than about 0.8, less than about 0.7, less than about 0.6, less than about 0.5, less than about 0.4, or less than about 0.3. In some embodiments, the input stream has a ratio of alkane/$CO_2$ of greater than about 1.0, greater than about 1.1, greater than about 1.2, greater than about 1.3, greater than about 1.4, greater than about 1.5, greater than about 1.6, greater than about 1.7, greater than about 1.8, greater than about 1.9, greater than about 2.0, greater than about 2.1, greater than about 2.2, greater than about 2.3, greater than about 2.4, or greater than about 2.5. In some embodiments, the input stream has a ratio of alkane/$CO_2$ of about 3.0, about 2.9, about 2.8, about 2.7, about 2.6, about 2.5, about 2.4, about 2.3, about 2.2, about 2.1, about 2.0, about 1.9, about 1.8, about 1.7, about 1.6, about 1.5, about 1.4, about 1.3, about 1.2, about 1.1, about 1.0 (i.e., stochiometric conditions), about 0.9, about 0.8, about 0.7, about 0.6, about 0.5, about 0.4, about 0.3, or about 0.2, or any range within any two of these values.

In some embodiments, the olefin production rate increases as the ratio of alkane/$CO_2$ is increased due the non-oxidative dehydrogenation pathway (reaction 6). In some embodiments, the olefin production rate may be greater than about $0.5 \times 10^{-2}$ mol gcat$^{-1}$ h$^{-1}$, greater than about $0.6 \times 10^{-2}$ mol gcat$^{-1}$ h$^{-1}$, greater than about $0.7 \times 10^{-2}$ mol gcat$^{-1}$ h$^{-1}$, greater than about $0.8 \times 10^{-2}$ mol gcat$^{-1}$ h$^{-1}$, greater than about $0.9 \times 10^{-2}$ mol gcat$^{-1}$ h$^{-1}$, greater than about $1.0 \times 10^{-2}$ mol gcat$^{-1}$ h$^{-1}$, greater than about $1.1 \times 10^{-2}$ mol gcat$^{-1}$ h$^{-1}$, greater than about $1.2 \times 10^{-2}$ mol gcat$^{-1}$ h$^{-1}$, greater than about $1.3 \times 10^{-2}$ mol gcat$^{-1}$ h$^{-1}$, greater than about $1.4 \times 10^{-2}$ mol gcat$^{-1}$ h$^{-1}$, or greater than about $1.5 \times 10^{-2}$ mol gcat$^{-1}$ h$^{-1}$, at a temperature of between 450° C. to about 700° C. In some embodiments, the selectivity of olefins is greater than 50%, greater than 60%, greater than 70%, greater than 80%, greater than 90%, greater than 95%, greater than 98%, or greater than 99% at a temperature of between 450° C. to about 700° C.

Another aspect of the invention is a system for ODH of alkanes. In some embodiments, ODH of alkanes is performed using a catalytic membrane reactor (CMR). The CMR comprises the bifunctional catalyst, disclosed herein, and a hydrogen selective membrane. In some embodiments, the reactor may be a fixed bed reactor or a packed bed reactor, where the catalyst bed is at least partially enclosed by a hydrogen selective membrane. Alternatively, the bifunctional catalyst may be wash-coated on the hydrogen selective membrane wall.

FIG. 2 shows a schematic of an embodiment of a CMR. The reactor comprises a packed catalyst bed that is enclosed in a hydrogen selective membrane. The reactor is housed in an enclosure to accommodate the $H_2$ that passes through the hydrogen selective membrane. The enclosure may be swept with a gas or a light vacuum may be applied to remove the hydrogen from the enclosure. The ODH step to produce olefin(s) takes place on metal oxide catalyst (e.g., $Cr_2O_3$). The unwanted co-products CO and $H_2O$ are converted to $CO_2$ and $H_2$ over the WGS active ceramic support (e.g., BZY). The $H_2$ is removed from the catalyst bed through a $H_2$-selective membrane thus shifting the WGS equilibrium to convert more CO to $CO_2$, but also producing $H_2$. After separation, the hydrogen may be captured and stored in a container or on a sorbent (contained in the outer enclosure or downstream of the outer enclosure) or it may used in other downstream processes. Likewise, the other reaction products, other than hydrogen, may be captured and stored, or used in other downstream processes.

In some embodiments, the hydrogen selective membrane fully or at least partially encloses the catalyst bed. The hydrogen selective membrane may be selected from a metal, a ceramic, a polymer, and combinations thereof. Suitable hydrogen selective membranes are thin-film Pd and Pd alloys that are supported in or on porous-ceramic structures. In these membranes, $H_2$ flux is driven by $H_2$ partial pressure differences across the membrane. This information is set forth in H. W. Abu El Hawa, S. N. Paglieri, C. C. Morris, A. Harale, and J. D. Way, "Application of a Pd—Ru composite membrane to hydrogen production in a high temperature membrane reactor," *Sep. Purif. Technol.*, 147: 388-397, 2015 (incorporated herein by reference in its entirety). Other suitable membrane are protonic ceramic membranes, such as for example, membranes based on doped barium zirconates and cerates that are proton conductors, where the effective $H_2$ flux is controlled by combinations of $H_2$ partial pressure and an imposed voltage. Ohmic heating associated with proton conduction could play a role in the reactor thermal balance. This information is set forth in H. Zhu, S. Ricote, C. Duan, R. P. O'Hayre, D. S. Tsvetkov, and R. J. Kee, "Defect incorporation and transport with $BaZr_{0.8}Y_{0.2}O_{3-\delta}$ (BZY20) proton-conducting membranes," *J. Electrochem. Soc.*, 165: F581-F588, 2018; and H. Zhu, S. Ricote, C. Duan, R. P. O'Hayre, and R. J. Kee, "Defect chemistry and transport within dense $BaCe_{0.7}Zr_{0.1}Y_{0.1}Yb_{0.1}O_{3-\delta}$ (BCZYYb) proton-conducting membranes," *J. Electrochem. Soc.*, 165: F845-F853, 2018 (each of which are incorporated herein by reference in their entirety).

The removal of $H_2$ from the pore volume of the bifunctional catalyst is important because $H_2$ inhibits olefin formation. Removal of $H_2$ from the catalyst bed enhances both the WGS and non-oxidative dehydrogenation pathway. In a typical ODH process over a redox active metal-oxide catalyst, the rate limiting step is the activation of alkane via MvK cycle. In other words, the catalytic activity is determined by the available lattice oxygen supplied by the metal-oxide catalyst. This step is kinetically controlled, and lattice oxygen concentration increases with increasing redox activity at high temperatures. Thus, the ODH operating temperature is highly controlled by the available lattice oxygen in metal-oxide catalyst. The catalytic membrane reactor increases the lattice oxygen concentration by shifting the equilibrium of reaction 4; more lattice oxygen is generated at lower reaction temperatures where redox activity is limited (e.g., $T \leq 450°$ C. for $Cr_2O_3$). Hence, the membrane integrated ODH process can operate at lower temperatures compared to a packed-bed operation. Because use of a catalytic membrane reactor can decrease the ODH reaction temperature, the catalyst durability or stability is improved. At relatively low temperatures (of about 500° C. to about 550° C.) olefin dehydrogenation to coke, via the Boudouard reaction (reaction 8), and aromatization pathways to undesirable PAHs can be impeded or avoided. Further, use of a catalytic membrane reactor produces two valuable product streams, olefin(s) and pure $H_2$.

The CMR reactor may comprise at least one input gas stream and at least two output gas streams, one for the separated hydrogen gas and the other for at least one of the other reaction products. The flow through the reactor may be characterized as plug flow or parabolic flow. The Gas Hourly Space Velocity (GHSV) may range from about 10,000 $h^{-1}$ to about 50,000 $h^{-1}$. In some embodiments, the GHSV may be about 10,000 $h^{-1}$, about 15,000 $h^{-1}$, about 20,000 $h^{-1}$, about 25,000 $h^{-1}$, about 30,000 $h^{-1}$, about 35,000 $h^{-1}$, about 40,000 $h^{-1}$, about 45,000 $h^{-1}$, or about 50,000 $h^{-1}$, or any range within any two of these values.

In some embodiments, the reactor may comprise one or more reactor tubes and/or one or more hydrogen selective membranes. The reactor may further comprise a means for controlling and/or measuring the input gas flow rate, the output gas flow rate, the temperature, and the pressure. The reactor may comprise a means for measuring the presence of and/or the concentration of one or more components of the input gas stream and/or output gas stream (e.g., FTIR, HPLC, or other analytic means). The reactor may comprise a means for collecting the hydrogen gas stream and a means for collecting the olefins.

Example 1: Preparation of Bifunctional Catalyst

The BZY ($BaZr_{0.85}Y_{0.15}O_{3-\delta}$) support was prepared using calcination of nitrate precursors. The metal precursors were $Ba(NO_3)_2$ (Alfa Aesar, 99% purity), $ZrO(NO_3)_2$ (Sigma Aldrich, 99% purity), and $Y_2O_3$ (Alfa Aesar, 99.9% purity). Complexing agents were ethylenediaminetetraacetic acid (EDTA, Alfa Aesar, 99.4% purity), citric acid (Alfa Aesar, 99% purity), nitric acid (Sigma Aldrich, 99.999% purity), and ammonium hydroxide (VWR Analytical, 38-30% concentration). Powders were produced utilizing a slightly modified EDTA-citrate complexing synthesis method. In this method, stoichiometric amounts of nitrate metal cation precursors were combined with a sufficient amount of EDTA and citric acid to ensure complete cation mixing. The molar ratio of EDTA to citric acid to BZY powder was 2.5:1.2:1. After adding yttria that was dissolved in a heated solution of water and nitric acid, the solution was heated to 325° C. while adding ammonium hydroxide to reduce the pH of the solution. The solution was then stirred and heated continuously until a sticky gel was formed. The gel was subsequently transferred to a drying oven at 150° C. for 12 hours. The result was a BZY char that was then calcined at 900° C. for 10 hours, producing as-calcined powder with an average particle diameter of 40 nm.

Bifunctional catalysts were prepared using the incipient wetness impregnation technique. Metal nitrate salts and either gamma alumina powder or BZY powder were premixed and diluted with water. The resulting solution was dried overnight at 80° C. while stirring. Finally, the catalyst was calcined at 500° C. for 5 hours in air.

Figure 3:
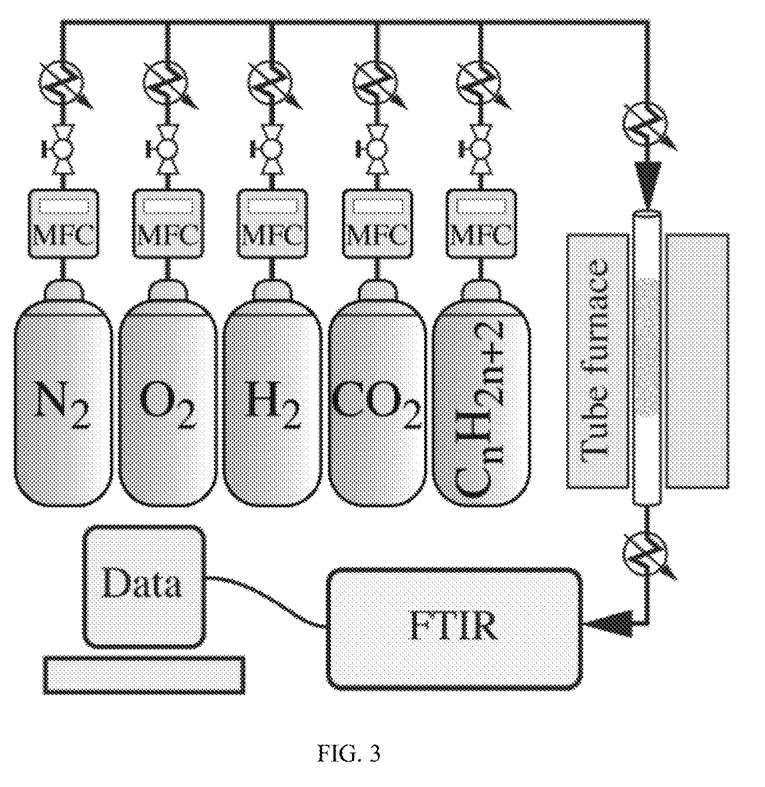
FIG. 3: A schematic representation of a catalyst test system using a packed bed reactor.

Example 2: Oxidative Dehydrogenation of $C_3H_8$ Using a $Cr_2O_3/Al_2O_3$ Catalyst The oxidative dehydrogenation performance of a $Cr_2O_3/Al_2O_3$ catalyst was evaluated using a laboratory-scale packed-bed reactor, a schematic of which is shown in FIG. 3. The catalyst particles were sieved into the 125-250 μm range. Then 0.5 grams of the $Cr_2O_3/Al_2O_3$ catalyst was mixed with 0.5 grams quartz sand (125-250 μm range) and packed in a 10 mm OD, 7 mm ID quartz reactor. The catalyst was sandwiched between quartz wool and housed in a horizontal furnace. The reaction temperature was controlled via two K-type thermo-couples, positioned before and after the catalyst bed. The flow rates of the feed gases ($C_3H_8$, $CO_2$, $H_2$, $N_2$, and $O_2$) were established via mass flow controllers (MFC, Bronkhorst) and the gasses were pre-mixed before entering the reactor. The inlet and outlet lines were heated to 130° C. to avoid any condensation. The reactor outlet gas composition was measured by an online Fourier-transform infrared spectrometer (FTIR, Multigas MG2030, MKS). The experiments were conducted over a range of flow rates, temperature, and $C_3H_8/CO_2/H_2/N_2$ ratios. The reported conversions, rates, and selectivities are average steady-state values within 10-minute measurement intervals.

Figure 4A:
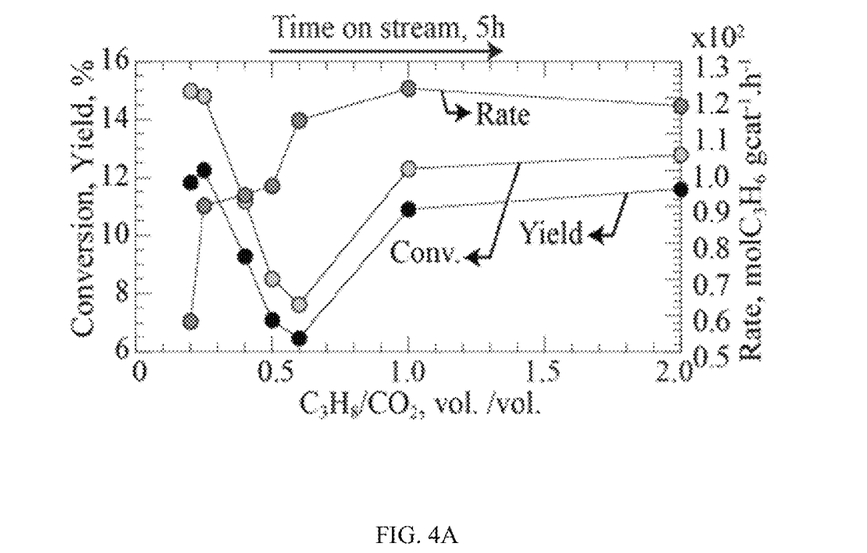

FIG. 4A shows propane dehydrogenation at 600° C. using a $Cr_2O_3/Al_2O_3$ catalyst, as a function of $C_3H_8/CO_2$ ratio. The data show two distinct regions where high $C_3H_8$ conversion is possible. Under very $C_3H_8$-lean conditions (i.e., $C_3H_8/CO_2 \leq 0.3$), high levels of $C_3H_8$ conversion are obtained, but overall olefin production rates are low. The process behavior changes as the feed mixture becomes more $C_3H_8$ rich. The conversion and yield initially drop sharply as $C_3H_8/CO_2$ is increased before undergoing an abrupt recovery and stabilizing in the regime $1 \leq C_3H_8/CO_2 \leq 2.5$. A benefit of operating under propane rich conditions is the increased $C_3H_6$ production rate, which is approximately 0.01 mol $gcat^{-1}$ $h^{-1}$, which is an order of magnitude more than previously reported in the literature.

Figure 4B:
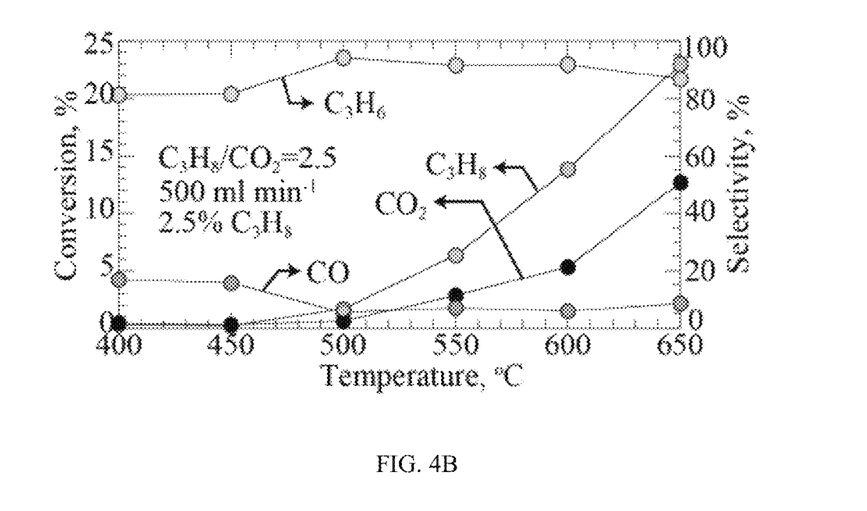

FIG. 4B displays the temperature dependence of $C_3H_8$ and $CO_2$ conversion and product selectivity for a fixed $C_3H_8/CO_2$ ratio of 2.5. Across the entire range examined, the selectivity to $C_3H_6$ is excellent (80-90%). Moreover, catalytic activity is negligible below 450° C., before increasing significantly with temperature. However, simply increasing temperature is detrimental for catalyst stability because above 600° C. as the olefin product(s) continue to dehydrogenate to form coke or polyaromatic hydrocarbons. A final important observation is that $CO_2$ conversion lags propane conversion. The data in FIG. 4B infers that the WGS and thermal cracking side reactions likely compete with the desired ODH reaction.

Figure 5A:
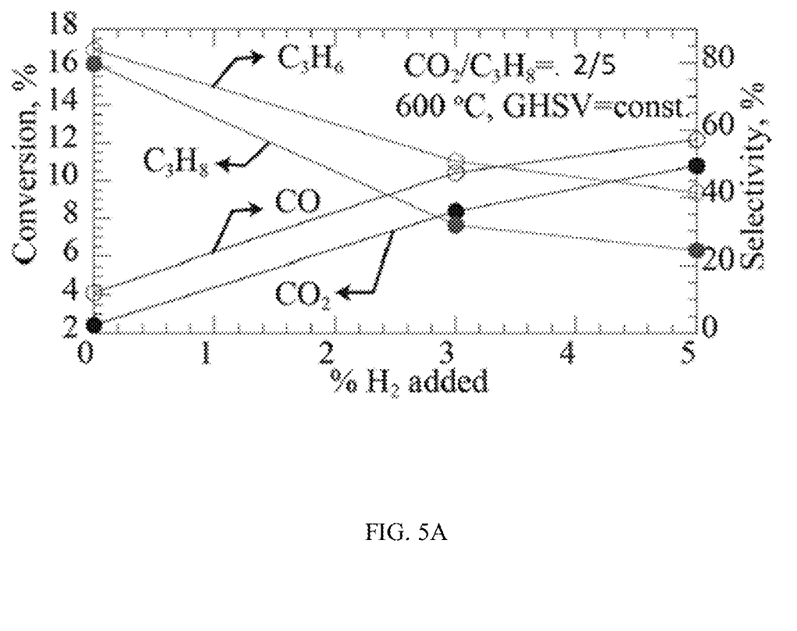

Example 3: Impact of $H_2$ Concentration on the ODH of $C_3H_8$ Using a $Cr_2O_3/Al_2O_3$ Catalyst The impact of $H_2$ concentration on the $C_3H_8$ conversion and selectivity was examined for a fixed $C_3H_8/CO_2$ ratio of 2.5, using the reactor configuration and procedure described in Example 2. FIG. 5A shows of the impact of $H_2$ addition to the $C_3H_8/CO_2$ reactive gas mixture at 600° C., while keeping the total flow rate constant. Both the $C_3H_8$ conversion and selectivity to $C_3H_6$ decrease substantially as $H_2$ is added to the system. In contrast, the $CO_2$ conversion and CO selectivity increase. This is direct evidence that, in the presence of $H_2$, the reverse water gas shift (rWGS) pathway dominates over the ODH pathway.

Figure 5B:
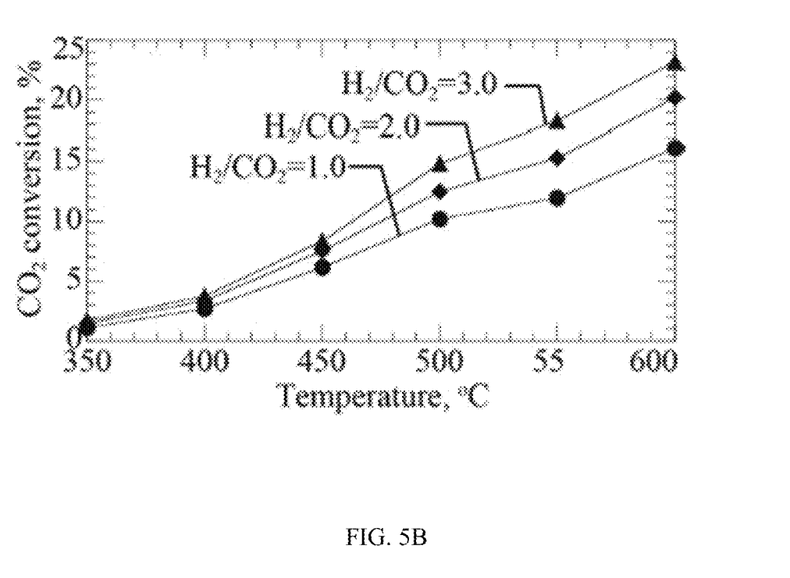

If $H_2$ addition decreases the ODH activity, it is expected that $H_2$ removal via a $H_2$-selective membrane can increase the olefin selectivity and conversion. The ODH process requires replenishing the lattice oxygen via rWGS step. Thus, the rWGS activity of the catalyst determines the overall ODH activity. FIG. 5B shows that the $Cr_2O_3/Al_2O_3$ catalyst is in fact a good rWGS catalyst as well. $CO_2$ hydrogenation activity over $Cr_2O_3/Al_2O_3$ catalyst highly depends on the temperature. Below 450° C., the catalytic activity is independent of the $CO_2/H_2$ ratios and conversion is limited by the redox activity. However above 450° C., the catalytic activity highly depends on the partial pressure of $H_2$. Under the desired operating conditions for ODH (450-550° C.) it is plausible that rWGS and ODH reaction co-exist. For all cases, $H_2O$ and CO are produced at equal rates. The CO selectivity is found to be ≥99.9%, and the only by-product detected is negligible amounts of $CH_4$. Thus, the $Cr_2O_3/Al_2O_3$ catalyst is highly selective to CO formation when $H_2$ co-exists with $CO_2$.

Example 4: Oxidative Dehydrogenation of $C_3H_8$ Using a $Cr_2O_3$/BZY Catalyst

Figure 6:
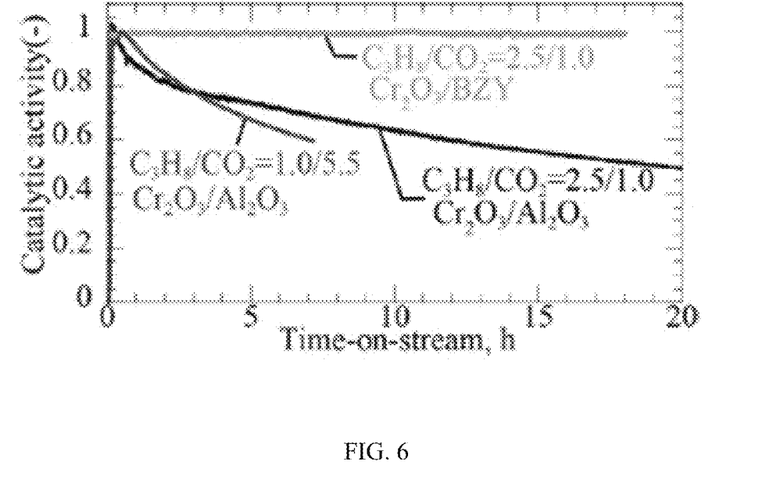
FIG. 6: Normalized catalytic activity for $Cr_2O_3$/BZY and $Cr_2O_3/Al_2O_3$ catalysts for propane conversion at T=600° C.

The oxidative dehydrogenation performance of a $Cr_2O_3$/BZY catalyst was evaluated in a laboratory-scale packed-bed reactor using the same procedure that was described in Example 2. FIG. 6 compares the catalytic activity of the $Cr_2O_3$/BZY catalyst versus the $Cr_2O_3/Al_2O_3$ catalyst at 600° C., at a $C_3H_8/CO_2$ ratio of 2.5. Results are also shown for the $Cr_2O_3/Al_2O_3$ under $C_3H_8$-lean conditions of $C_3H_8/CO_2$ of about 0.2. The BZY support delivers remarkable stability under $C_3H_8$-rich conditions. The $Cr_2O_3/Al_2O_3$ catalyst loses catalytic activity within a few hours, independent of the $CO_2$ content. In fact, looking more carefully, under $C_3H_8$-lean operating conditions the fouling rate is further increased. The catalytic activity is slightly better within the first three hours for $C_3H_8$-lean conditions but then a sharp decay follows. This could be due to the high CO content, which enhances the Boudouard reaction.

Accordingly, the compositions, apparatus, systems, and methods of the present disclosure have been described with some degree of particularity directed to the exemplary embodiments of the present disclosure. It should be appreciated though that modifications or changes may be made to the exemplary embodiments of the present disclosure without departing from the inventive concepts contained herein. Various modifications of the above-described invention will be evident to those skilled in the art. It is intended that such modifications are included within the scope of the following claims.

The invention claimed is:

1. A bifunctional oxidative dehydrogenation catalyst comprising a metal oxide and a redox active ceramic support, wherein the redox active ceramic support promotes a water-gas shift process, and wherein the redox active ceramic support comprises a doped perovskite ceramic.

2. The bifunctional oxidative dehydrogenation catalyst according to claim 1, wherein the metal oxide is selected from the group consisting of $Cr_2O_3$, $V_2O_5$, $In_2O_3$, $Fe_2O_3$, and combinations thereof, and wherein the metal oxide is mixed with or impregnated in the redox active ceramic support.

3. The bifunctional oxidative dehydrogenation catalyst according to claim 1, wherein the redox active ceramic support comprises one or more of $Al_2O_3$, $Ce_2O_3$, $ZrO_2$, $BaCe_{0.7}Zr_{0.1}Y_{0.1}Yb_{0.1}O_{2.95}$, and $BaZr_{1-x}Y_xO_{3-\delta}$ ($0 \leq x \leq 0.20$).

4. The bifunctional oxidative dehydrogenation catalyst according to claim 1, wherein the metal oxide promotes alkane dehydrogenation via a Mars van Krevelen process with carbon dioxide as an oxidant.

5. A method for alkane dehydrogenation, comprising:
providing a catalytic membrane reactor comprising a catalyst bed and a hydrogen selective membrane, wherein the catalyst bed comprises a bifunctional catalyst comprising a metal oxide and a redox active ceramic support, and wherein the redox active ceramic support comprises a doped perovskite ceramic, contacting an input gas stream comprising at least one alkane and carbon dioxide with the bifunctional catalyst to form a product gas stream comprising at least one olefin and hydrogen, and separating the hydrogen from the product gas stream.

6. The method according to claim 5, wherein the metal oxide is selected from the group consisting of $Cr_2O_3$, $V_2O_5$, $In_2O_3$, $Fe_2O_3$, and combinations thereof, and wherein the metal oxide is mixed with or impregnated in the redox active ceramic support.

7. The method according to claim 5, wherein the redox active ceramic support comprises one or more of $Al_2O_3$, $Ce_2O_3$, $ZrO_3$, $BaCe_{0.7}Zr_{0.1}Y_{0.1}Yb_{0.1}O_{2.95}$, and $BaZr_{1-x}Y_xO_{3-\delta}$ ($0 \leq x \leq 0.20$).

8. The method according to claim 5, wherein the at least one alkane comprises ethane, propane, butane, or mixtures thereof.

9. The method according to claim 5, wherein alkane dehydrogenation occurs at least partially via a Mars van Krevelen process and wherein a water-gas shift process forms at least some of the carbon dioxide.

10. The method according to claim 5, wherein a molar ratio of the at least one alkane to carbon dioxide in the input gas stream is greater than 1.

11. The method according to claim 5, wherein the contacting step occurs at a temperature from about 450° C. to about 650° C.

12. The method according to claim 5, wherein the hydrogen selective membrane comprises a material selected from the group consisting of a metal, a ceramic, a polymer, and combinations thereof.

13. The method according to claim 5, wherein a rate of olefin production is about $1.0 \times 10^{-2}$ mol $gcat^{-1}$ $h^{-1}$ or more.

14. A catalytic membrane reactor comprising:

a. a bifunctional catalyst comprising a metal oxide and a redox active ceramic support, wherein the redox active ceramic support comprises a doped perovskite ceramic; and b. a hydrogen selective membrane, wherein the bifunctional catalyst is contained in a catalyst bed that is at least partially enclosed by the hydrogen selective membrane.

15. The catalytic membrane reactor of claim 14, wherein the hydrogen selective membrane comprises a material selected from the group consisting of a metal, a ceramic, a polymer, and combinations thereof.

16. The catalytic membrane reactor of claim 14, wherein the metal oxide is selected from the group consisting of $Cr_2O_3$, $V_2O_5$, $In_2O_3$, $Fe_2O_3$, and combinations thereof, and wherein the metal oxide is mixed with or impregnated in the redox active ceramic support.

17. The catalytic membrane reactor of claim 14, wherein the redox active ceramic support comprises one or more of $Al_2O_3$, $Ce_2O_3$, and $ZrO_2$.

18. The catalytic membrane reactor of claim 14, further comprising an input gas stream and first and second output gas streams, the input gas stream comprising carbon dioxide and at least one alkane, the first output gas stream comprising at least one olefin, and the second output gas stream comprising hydrogen.

* * * * *